United States Patent [19]
Yates

[11] Patent Number: 5,891,863
[45] Date of Patent: *Apr. 6, 1999

[54] ALENDRONATE THERAPY TO PREVENT LOOSENING OF, OR PAIN ASSOCIATED WITH, ORTHOPEDIC IMPLANT DEVICES

[75] Inventor: Ashley J. Yates, Westfield, N.J.

[73] Assignee: Merck & Co., Inc., Rahway, N.J.

[*] Notice: The term of this patent shall not extend beyond the expiration date of Pat. No. 5,646,134.

[21] Appl. No.: 876,898

[22] Filed: Jun. 16, 1997

Related U.S. Application Data

[63] Continuation of Ser. No. 230,670, Apr. 21, 1994, Pat. No. 5,646,134.

[51] Int. Cl.$^6$ .................................................. A61K 31/66
[52] U.S. Cl. ............................................................ 514/108
[58] Field of Search .............................................. 514/108

[56] References Cited

U.S. PATENT DOCUMENTS

| | | | |
|---|---|---|---|
| 4,753,652 | 6/1988 | Langer et al. | 623/1 |
| 5,270,365 | 12/1993 | Gertz et al. | 514/108 |
| 5,646,134 | 7/1997 | Yates | 514/108 |

FOREIGN PATENT DOCUMENTS

| | | |
|---|---|---|
| 0 094 714 A3 | 11/1993 | European Pat. Off. . |
| WO 94/14455 | 7/1994 | WIPO . |
| WO 94/21266 | 9/1994 | WIPO . |
| WO 94/23770 | 10/1994 | WIPO . |
| WO 95/30421 | 11/1995 | WIPO . |

OTHER PUBLICATIONS

Finerman, et al., 1981, Metabolic Bone Disease & Related Res. 3(4&5): 337–42.
(Abstract) Passeri, M., 1992, Ann. Ital. Med. Int. 7 (3 Suppl.):137S–153S.
Dustmann et al., 1988, Z. Orthop. 126(3):314–25.
Suva et al., Journal of Bone and Mineral Res., vol. 8, No. 3, pp. 379–388 (1993).

*Primary Examiner*—Theodore J. Criares
*Attorney, Agent, or Firm*—Anthony D. Sabatelli; Melvin Winokur

[57] ABSTRACT

Disclosed is a therapy for treating and for preventing periprosthetic bone loss by the administration of a bisphosphonate bone resorption inhibitor, e.g., alendronate, in patients who have an orthopedic implant device.

4 Claims, 1 Drawing Sheet

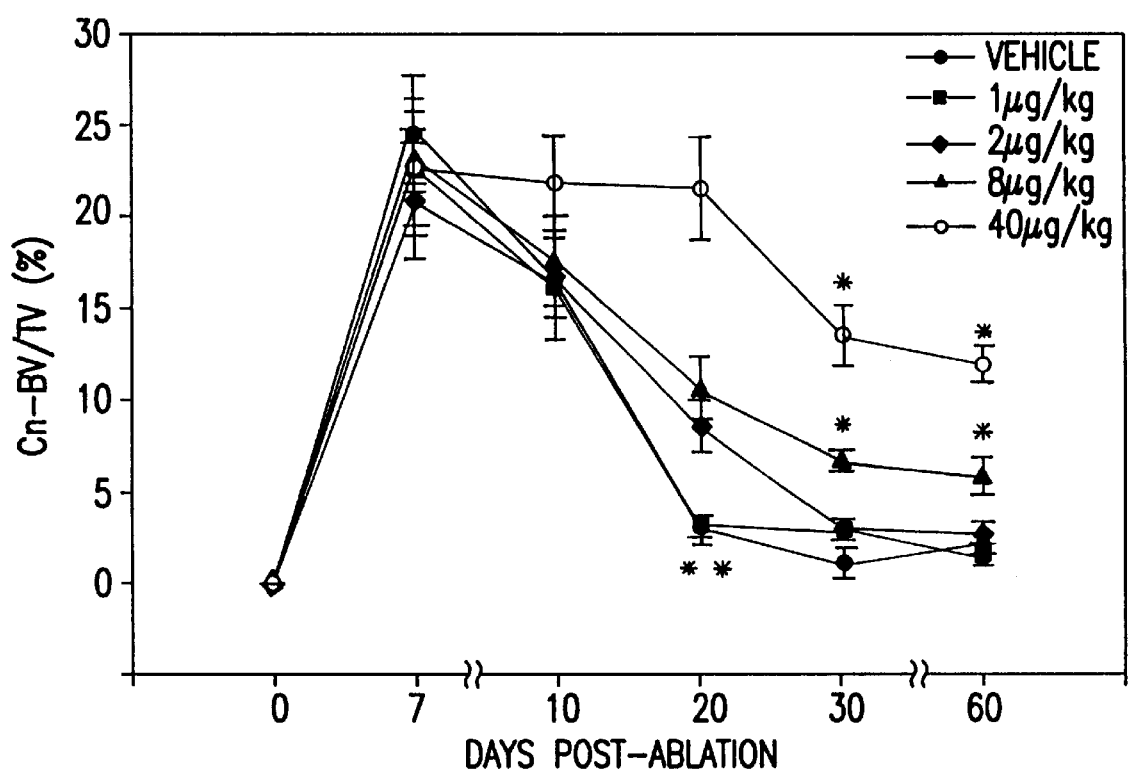
FIG.

ALENDRONATE THERAPY TO PREVENT LOOSENING OF, OR PAIN ASSOCIATED WITH, ORTHOPEDIC IMPLANT DEVICES

CROSS REFERENCE TO RELATED APPLICATIONS

This is a continuation of application Ser. No. 08/230,670, filed Apr. 21, 1994, now U.S. Pat. No. 5,646,134.

FIELD OF THE INVENTION

The instant invention relates generally to the use of alendronate to prevent periprosthetic bone loss in patients having an orthopedic implant device.

BACKGROUND OF THE INVENTION

A major problem with patients who have orthopedic implant devices or joint prosthesis, such as hip replacements, is that many of these begin to fail after five years or so from the time that they are inserted. The failure rate increases exponentially with time so that many patients with an aging hip prosthesis (10 to 15 years), experience pain at the site of the implant and eventually require revision to the original procedure. Although initially this was considered to be a result of fragmentation of the cement substances utilized in older hip prostheses, the problem continues to be observed even in the newer devices which do not rely on the use of cement. A hallmark of these patients is that at the time they develop pain and loosening of the joint they have markedly increased bone turnover, especially bone resorption, in the bone immediately adjacent to the implant. Evidence for this bone turnover can be seen from the fact that bone scanning agents, which are bisphosphonates tagged with technetium, are often taken up at very high concentrations in these areas indicating that there may well be significant targeting of bisphosphonates to the periprosthetic bone.

There is a need in the art for localized controlled/extended release dosage forms of bone growth promotant since in the United States, there are approximately 5 million fractures and 265,000 prosthetic implants per year. Of this population, there is about a 20–30% failure rate within five years of the operation, requiring a repeat surgery and device implant.

Normal bones are living tissues which undergo constant resorption and new bone formation, with the net effect of maintenance of a constant mineral balance. The dual process is commonly called "bone turnover". In normal growing bones, the mineral deposition exceeds the mineral resorption, whereas in certain pathological conditions, bone resorption exceeds bone deposition, for instance due to malignancy or primary hyperparathyroidism, or in osteoporosis. In other pathological conditions the deposition of new bone may take place in undesirable amounts and areas leading to e.g. heterotopic ossification, osteosclerosis, and Paget's disease which is a combination of an abnormal high bone resorption followed by an abnormal calcium deposition. With orthopedic implants, bone resorption may occur at an accelerated rate in the periprosthetic area leading to net bone loss.

Most of the currently available therapeutic agents for the treatment of osteoporosis, e.g. estrogens, act by reducing bone resorption in the osteoporotic patient. See the review article, "British Medical Bulletin" 46 (1), p. 94–112 (1990).

Bisphosphonates are also known in the art as bone resorption inhibitors.

Alendronate, 4-amino-1-hydroxybutylidene-1,1-bisphosphonic acid monosodium trihydrate is a known bone resorption inhibitor and is described in U.S. Pat. Nos. 4,922,007 and 5,019,651 (Merck).

Clodronate, (dichloromethylene)bisphosphonic acid disodium salt (Proctor and Gamble, is described in Belgium Patent 672,205 (1966) and its preparation is found in *J. Org. Chem* 32, 4111 (1967).

Tiludronate, ([(4-chlorophenyl)thiomethylene] bisphosphonic acid) (Sanofi) is described in U.S. Pat. No. 4,876,248 issued Oct. 24, 1989.

YM 175 ([(cycloheptylamino)methylene]bisphosphonic acid, disodium salt) by Yamanouchi is described in U.S. Pat. No. 4,970,335 issued Nov. 13, 1990.

BM 21.0995 (1-Hydroxy-3-(methylpentylamino)-propylidene-bisphosphonate) by Boehringer-Mannheim—is described in U.S. Pat. No. 4,927,814 issued May 22, 1990.

A study by Proctor and Gamble (Norwich Eaton Pharmaceuticals) using risedronate, whose chemical name is sodium trihydrogen [1-hydroxy-2-(3-pyridinyl)ethylidene] bisphosphonate, in combination with estrogen showed a positive effect on bone loss in ovariectomized rats (published in Abstracts 731 and 732 at the Fall 1992 ASBMR meeting in Minnesota).

The article, "J. Clin. Invest.", January 1992, 89 (1), p. 74–78 by J. Chow et al., describes the effect of estrogen on ovariectomized rats in which bone resorption was suppressed by pamidronate whose chemical name is 3-amino-1-hydroxy propylidene-bisphosphonic acid disodium salt. They concluded that estrogen inhibits bone resorption and also stimulates bone formation.

Another Proctor and Gamble compound, piridronate, [2-(2-pyridinyl)ethylidene]-bisphosphonic acid, monosodium salt is described in U.S. Pat. No. 4,761,406 as having bone resorption inhibition activity.

The article, "Monatschefte" 99, 2016 (1968) by F. Kasparet describes the synthesis of etidronate, (1-hydroxyethylidene)-bisphosphonic acid, disodium salt, (Proctor and Gamble).

However, the above cited art does not suggest or describe the use of a bisphosphonate in situations to specifically prevent bone resorption in the periprosthetic bone area of an orthopedic implant device.

What is desired in the art is a therapy to optimally treat the bone resorption in the periprosthetic area of an implant device i.e., the bone area which is in contact and close proximity to the device implant, to retard the loosening of the device and to alleviate the pain associated with this condition.

SUMMARY OF THE INVENTION

We have discovered that a bisphosphonate can be used in such patients for the prophylaxis and treatment of failure of joint prostheses, e.g. for the hip or knee. Long term administration of a relatively low dose of a bisphosphonate, e.g., alendronate, can prevent the periprosthetic bone resorption process and thereby maintain the integrity of the total structure.

The treatment can be further extended to patients with symptomatic failure of a joint prostheses or internal fixation device. Bisphosphonates, e.g., alendronate, are able to reverse the loosening of a prosthesis once it has occurred, and there is also some alleviation of the bone pain which accompanies this complication of joint replacement.

By this invention there is provided a method for treating and/or preventing (reducing the risk of) periprosthetic bone loss in a subject having an orthopedic implant device comprising administering to said subject a pharmaceutically effective dose of a bisphosphonate. The bisphosphonate applicable in the method includes: alendronate, clodronate, tiludronate, YM 175, BM 21.0995, etidronate, risedronate, piridronate, pamidronate, or combinations thereof.

BRIEF DESCRIPTION OF THE FIGURE

The Figure illustrates the effects of alendronate on bone resorption at different concentrations, on the rat bone marrow ablation model in which bone is regenerated in the voided regions of the bone.

Data represent mean±SEM (n=4–6). The asterisk "*" indicates significantly different from vehicle, 1 μg/kg and 2 μg/kg alendronate treated groups (Fisher PLSD, p<0.05). The double asterisk "**" indicates vehicle and 1 μg/kg alendronate treated groups significantly different from all other groups (Fisher PLSD, p<0.05).

DETAILED DESCRIPTION OF THE INVENTION AND PREFERRED EMBODIMENTS

The bisphosphonates described above are useful in the invention process. Preferred are residronate, clodronate, tiludronate and alendronate and particularly preferred is alendronate.

The method disclosed herein can be used to treat human subjects who have a prosthesis, i.e., a medical implant device.

The method involves the administration of a bisphosphonate in an osteogenically effective amount to inhibit bone resorption in the periprosthetic bone area of a medical implant device.

By the term "periprosthetic bone area" as used herein is meant the area of bone which is an contact with the medical implant device or in the immediate proximity thereof.

The term "inhibition of bone resorption" as used herein refers to prevention of bone loss, especially the inhibition of removal of existing bone either from the mineral phase and/or the organic matrix phase, through direct or indirect alteration of osteoclast formation or activity. Thus, the term "inhibitor of bone resorption" as used herein refers to agents that prevent bone loss by the direct or indirect alteration of osteoclast formation or activity.

The term "osteogenically effective" as used herein means that amount which decreases the turnover of mature bone. As used herein, an osteogenically effective dose is also "pharmaceutically effective."

The term "subject" as used herein refers to a living vertebrate animal such as a mammal in need of treatment, i.e., in need of periprosthetic bone repair. The periprosthetic bone loss may arise in cases of systemic bone disease, as in osteoporosis (of any etiology), osteoarthritis, Paget's disease, osteomalacia, multiple myeloma and other forms of cancer.

The term "treatment" or "treating" as used herein shall mean (1) providing a subject with an amount of a bisphosphonate sufficient to act prophylactically on periprosthetic bone to prevent the development of a weakened and/or unhealthy state; and/or (2) providing a subject with a sufficient amount of a bisphosphonate so as to alleviate or eliminate a disease state and/or the symptoms of a disease state in the area of periprosthetic bone.

The methods of the invention are useful for treating defects and disorders in the periprosthetic area of bone which result in a weakened structure and/or pain.

In accordance with one method of use, the bisphosphonate may be administered to the periprosthetic bone area systemically either orally and/or parenterally, including subcutaneous or intravenous injection. Additionally, the bisphosphonate may be delivered in a slow release form from a suitable carrier.

In accordance with another method of use, the bisphosphonate may be administered locally to the specific periprosthetic area in need of bone growth or repair. Thus, the bisphosphonate may be implanted directly at the site to be treated, for example, by injection or surgical implantation in a sustained-release carrier. Suitable carriers include hydrogels, controlled- or sustained-release devices (e.g., an Alzet® minipump), polylactic acid, and collagen matrices. Presently preferred carriers are formulations of atelopeptide collagen containing particulate calcium phosphate mineral components, such combinations of homologous or xenographic fibrillar atelopeptide collagen (for example Zyderm® Collagen Implant, available from Collagen Corporation, Palo Alto, Calif.) with hydroxapatitetricalcium phosphate (HA-TCP, available from Zimmer, Inc., Warsaw, Ind.). It is presently preferred to administer implant compositions containing alendronate in a collagen/mineral mixture implant.

Bisphosphonate delivered in sustained-release vehicles is useful for improving implant fixation, for example, for improving in growth of new bone into a metal prosthesis in joint reconstruction or orthopedic implants.

Alternatively, orthopedic implants can be coated with bisphosphonate to enhance attachment of the implant device to the bone at the time of the implant operation.

In general, implant devices may be coated with a bisphosphonate as follows. The bisphosphonate is dissolved at a concentration in the range of 0.01 μg/ml to 200 mg/ml in phosphate-buffered saline (PBS) containing 2 mg/ml serum albumin. The porous end of an implant is dipped in the solution and is airdried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the bisphosphonate, is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the periprosthetic bony site immediately or is airdried and rehydrated with PBS prior to implanting, with the objective of maximizing new bone formation into and around the implant while minimizing the ingrowth of soft tissue into and around the implant site.

Pharmaceutical formulations of the invention which include a bisphosphonate inhibitor of bone resorption for administration will generally include an osteogenically effective amount of the bisphosphonate to promote bone growth, in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. The bisphosphonate inhibitor of bone resorption may also be delivered in a sustained release form from a suitable carrier.

A presently preferred vehicle comprises phosphate-buffered saline (PBS) or isotonic citrate buffer. A thorough discussion of suitable vehicles for parenteral administration may be found in E. W. Martin. "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

The precise dosage of bisphosphonate necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models, as described below. In general terms, an effective dose for biphosphonate is about 1.5 to 3000 μg/kg per day of body weight and preferably about 10 μg/kg to about 200 μg/kg per day of body weight. A particularly preferred dosage is 10 mg per day per person.

Effective doses for local administration will be about 0.001 μg to 1 mg per application site.

The pharmaceutical compositions according to the present invention containing bisphosphonate may be prepared for use in the form of capsules or tablets or in solution for oral administration or for systemic use. The compositions are advantageously prepared together with inert carriers such as sugars (saccharose, glucose, lactose), starch and derivatives, cellulose and derivatives, gums, fatty acids and their salts, polyalcohols, talc, aromatic esters.

Some typical pharmaceutical formulations containing alendronate, 4-amino-1-hydroxybutane-1,1-diphosphonic acid monosodium salt trihydrate, are shown here below:

ALENDRONATE TABLETS (WHITE), 200 MG

| INGREDIENT | COMPOSITION IN MG/TABLET | | | |
|---|---|---|---|---|
| | 2.5 mg* | 5.0 mg* | 10.0 mg* | 40.0 mg* |
| Alendronate | 3.26 | 6.55 | 13.05 | 51.21 |
| Lactose NF Anydrous | 113.74 | 110.45 | 103.95 | 64.79 |
| Microcrystalline Cellulose NF | 80.0 | 80.0 | 80.0 | 80.0 |
| Magnesium Stearate Impalpable NF | 1.00 | 1.00 | 1.00 | 1.00 |
| Croscarmellos Sodium NF Type A | 2.00 | 2.00 | 2.00 | 2.00 |

OPERCOLATED CAPSULES

| | 1 | 2 |
|---|---|---|
| Alendronate | mg 6.5 | mg 2.5 |
| Lactose | 110.0 | 110.0 |
| Avucek Ph101 | 80.0 | 80.0 |
| Aldisol/NF Type A | 2.0 | 2.0 |
| Magnesium Stearate | 1.0 | 1.0 |
| Total Weight | 202.5 Total Weight | 197.5 |

EFFERVESCENT GRANULATES

| | |
|---|---|
| Alendronate | mg 5.0 |
| Anhydrous Sodium Carbonate | 12.0 |
| Sodium Bicarbonate | 63.0 |
| Anhydrous Citric Acid | 110.0 |
| Sodium Saccharinate | 5.0 |
| Saccharose | 493.0 |
| Dehydrated Lemon Juice | 55.0 |
| Natural Essence of Lemon | 2.0 |
| Total Weight | 748 |

FORMULATIONS SUITABLE FOR INJECTION

| | | | | |
|---|---|---|---|---|
| Alendronate | mg | 0.5 | mg | 1.00 |
| Sodium Hydroxide | | 0.25 | | 0.25 |
| Sodium Chloride | | 8.40 | | 16.30 |
| Purified Water q h | ml | 1.0 | ml | 12.0 |

*Taken as the anhydrous monosodium salt-active ingredient.

Bisphosphonate drugs which prevent bone loss and/or add back lost bone can be evaluated in the ovariectomized rat. This animal model is well established in the art (see, for example, Wronski, et al. (1985) "Calcif. Tissue Int." 37:324–328; Kimmel, et al. (1990) "Calcif. Tissue Int." 46:101–110; and Durbridge, et al. (1990) "Calcif. Tissue Int." 47:383–387; these references are hereby incorporated in their entirety). Wronski, et al. ((1985) "Calcif. Tissue Int." 43:179–183)) describe the association of bone loss and bone turnover in the ovariectomized rat. Bisphosphonate drugs applicable in the instant invention are active in this assay.

EXAMPLE

Alendronate Effects on Bone Formation and Resorbability of Bone Formed During Alendronate Treatment To study the effects of alendronate during rapid bone formation, a modified bone marrow ablation model in the rat described in *J. Bone Miner. Res.* Vol. 8, pp. 379–388 (1993) by L. J. Suva et al., was used. In the rat, extraction of bone marrow (ablation) from a long bone results in rapid bone formation which fills 25% of the marrow cavity with cancellous bone (Cn) within 6 to 7 days. This bone is then fully resorbed (replaced) within the next 15 days. When rats were orally treated with 1, 2, 8 or 40 μg/kg alendronate day s.c. for 6 days, post-ablation, there was no difference in bone volume at 7 days (See the Figure), indicating that alendronate has no detectable effect on bone formation. In the Figure, Cn-BV/TV % represents cancellous bone volume divided by total structure volume; SEM represents standard error of the mean; ALN is alendronate; Fisher PLSD is a standard statistical least squares technique. After treatment was stopped, the amount of bone remaining in the marrow cavity at the various doses was examined at 4, 14, 24 and 54 days later. For an alendronate dose of 1 μg/kg, bone was completely resorbed at 14 days, no different from controls. At 2 μg/kg/day, bone was also completely resorbed 24 days after cessation of treatment. At 8 and 40 μg/kg/day, bone was also resorbed, albeit more slowly, resulting in a retention of about 33% and 50%, respectively, at 54 days (See the Figure). These findings show that, at levels much higher than a human dose, there is no interference at all with bone formation in this model, and that bone formed at these doses is fully resorbable, albeit more slowly than occurs with lower doses.

This data is consistent with the method of administering a bisphosphonate, e.g., alendronate, to a patient's periprosthetic bone area to prevent bone resorption and a weakening at the site of the medical implant device. The slowing of the rate of bone resorption, but not its complete inhibition, is predicted to be associated with an improvement in the local bone balance in the periprosthetic bone which would provide greater integrity to the overall bone and prosthesis structure.

What is claimed is:

1. A method of preventing loosening of an orthopedic prosthesis in a patient comprising administering to the patient a bone resorption inhibiting amount of a bisphosphonate selected from the group consisting of alendronate, clodronate, tiludronate, YM 175, BM 21.0995, etidronate, risedronate, piridronate, pamidronate, pharmaceutically acceptable salts thereof, and mixtures thereof.

2. A method of prevent loosening of a hip prosthesis in a patient comprising administering a bone resorption inhibiting amount of a bisphosphonate selected from the group consisting of alendronate, clodronate, tiludronate, YM 175, BM 21.0995, etidronate, risedronate, piridronate, pamidronate, pharmaceutically acceptable salts thereof, and mixtures thereof.

3. A method of preventing pain associated with loosening of an orthopedic prosthesis in a patient comprising administering to the patient a bone resorption inhibiting amount of a bisphosphonate selected from the group consisting of alendronate, clodronate, tiludronate, YM 175, BM 21.0995, etidronate, risedronate, piridronate, pamidronate, pharmaceutically acceptable salts thereof, and mixtures thereof.

4. A method of preventing pain associated with the loosening of a hip prosthesis in a patient comprising administering to the patient a bone resorption inhibiting amount of a bisphosphonate selected from the group consisting of alendronate, clodronate, tiludronate, YM 175, BM 21.0995, etidronate, risedronate, piridronate, pamidronate, pharmaceutically acceptable salts thereof, and mixtures thereof.

* * * * *